(12) United States Patent
Grady et al.

(10) Patent No.: US 10,987,010 B2
(45) Date of Patent: Apr. 27, 2021

(54) SYSTEMS AND METHODS FOR VASCULAR DIAGNOSIS USING BLOOD FLOW MAGNITUDE AND/OR DIRECTION

(71) Applicant: HeartFlow, Inc., Redwood City, CA (US)

(72) Inventors: Leo J. Grady, Millbrae, CA (US); Charles A. Taylor, Menlo Park, CA (US)

(73) Assignee: HeartFlow, Inc., Redwood City, CA (US)

( * ) Notice: Subject to any disclaimer, the term of this patent is extended or adjusted under 35 U.S.C. 154(b) by 72 days.

(21) Appl. No.: 14/691,105

(22) Filed: Apr. 20, 2015

(65) Prior Publication Data

US 2016/0220123 A1    Aug. 4, 2016

Related U.S. Application Data

(60) Provisional application No. 62/110,817, filed on Feb. 2, 2015.

(51) Int. Cl.
*A61B 5/026* (2006.01)
*A61B 5/00* (2006.01)
(Continued)

(52) U.S. Cl.
CPC .......... *A61B 5/026* (2013.01); *A61B 5/02028* (2013.01); *A61B 5/7246* (2013.01);
(Continued)

(58) Field of Classification Search
CPC ..... A61B 5/026; A61B 5/0261; A61B 5/0263; A61B 5/0265; A61B 5/027; A61B 5/0275;
(Continued)

(56) References Cited

U.S. PATENT DOCUMENTS 5,327,893 A * 7/1994 Savic ...................... A61B 8/06
600/454
5,441,052 A    8/1995 Miyajima
(Continued)

FOREIGN PATENT DOCUMENTS

WO    WO 2013/152395    * 10/2013    .............. A61B 6/00

OTHER PUBLICATIONS

Kotval et al. "Doppler diagnosis of partial vertebral/subclavian steals convertible to full steals with physiologic maneuvers." J Ultrasound Med. Apr. 1990;9(4):207-13.*

(Continued)

*Primary Examiner* — Meredith Weare
(74) *Attorney, Agent, or Firm* — Bookoff McAndrews, PLLC (57) ABSTRACT

Systems and methods are disclosed for diagnosing and treatment planning for vascular steal syndromes and retrograde flow. One method includes receiving a reference blood flow direction at a location in a reference vasculature; determining a patient-related blood flow direction at a location in a patient's vasculature corresponding to the location in the reference vasculature; determining a difference in direction, between the reference blood flow direction of the reference vasculature and the patient-related blood flow direction of the patient's vasculature; and generating a representation of the location in the patient's vasculature associated with the difference in direction between the reference blood flow direction and the patient-related blood flow direction, or generating a treatment recommendation for the patient's vasculature based on the difference in direction between the reference blood flow direction and the patient-related blood flow direction.

20 Claims, 5 Drawing Sheets

(51) Int. Cl.
  *A61B 8/06* (2006.01)
  *A61B 8/08* (2006.01)
  *G16H 50/50* (2018.01)
  *G16H 50/20* (2018.01)
  *A61B 5/02* (2006.01)

(52) U.S. Cl.
  CPC .......... *A61B 5/7275* (2013.01); *A61B 5/7278* (2013.01); *A61B 5/74* (2013.01); *A61B 8/06* (2013.01); *A61B 8/0891* (2013.01); *G16H 50/20* (2018.01); *G16H 50/50* (2018.01); *A61B 5/742* (2013.01); *A61B 8/488* (2013.01)

(58) Field of Classification Search
  CPC ... A61B 5/02755; A61B 5/028; A61B 5/0285; A61B 5/029; A61B 5/0295; G06F 19/3431; G06F 19/3437
  See application file for complete search history.

(56) References Cited

U.S. PATENT DOCUMENTS

| | | | | |
|---|---|---|---|---|
| 6,730,030 | B2* | 5/2004 | Palti | 600/441 |
| 8,315,812 | B2* | 11/2012 | Taylor | 702/19 |
| 8,523,779 | B2* | 9/2013 | Taylor et al. | 600/485 |
| 2007/0167751 | A1* | 7/2007 | Schilling | A61B 8/06 600/437 |
| 2008/0319308 | A1 | 12/2008 | Tang | |
| 2010/0241404 | A1* | 9/2010 | Taylor et al. | 703/1 |
| 2011/0213408 | A1 | 9/2011 | Gross | |
| 2012/0041739 | A1* | 2/2012 | Taylor | 703/11 |
| 2012/0059246 | A1* | 3/2012 | Taylor | 600/419 |
| 2012/0150516 | A1* | 6/2012 | Taylor et al. | 703/9 |
| 2012/0191467 | A1* | 7/2012 | LaPlante et al. | 705/2 |
| 2013/0172734 | A1* | 7/2013 | Hsieh | 600/425 |
| 2013/0246034 | A1 | 9/2013 | Sharma et al. | |
| 2014/0005535 | A1* | 1/2014 | Edie et al. | 600/427 |
| 2014/0066765 | A1* | 3/2014 | Fan et al. | 600/440 |
| 2014/0276027 | A1* | 9/2014 | Gaddis et al. | 600/427 |
| 2014/0354794 | A1* | 12/2014 | Imamura | A61B 5/0285 348/78 |
| 2015/0080686 | A1* | 3/2015 | Karlheinz | A61B 5/0071 600/317 |

OTHER PUBLICATIONS

K H Deeg et al.: "Pediatric Radiology Dopplersonographic diagnosis of sublavin steal in infants with coarctation of the aorta and interrupted aortic arch", Pediatric Radiology, vol. 19, No. 3, Mar. 1, 1989 (Mar. 1, 1989), pp. 163-166.

Meenakumari Ayekpam et al.: "Subclavian Steal Syndrome: A Case Report", Journal of Evolution of Medical and Dental Sciences, vol. 3, No. 73, Dec. 24, 2014 (Dec. 24, 2014), pp. 15461-15464.

International Search Report and Written Opinion for corresponding Application No. PCT/US2016/015987 dated Apr. 13, 2016, (14 pages).

Potter et al. "Subclavian Steal Syndrome." Circulation. 2014; 129: 2320-2323.

* cited by examiner

SYSTEMS AND METHODS FOR VASCULAR DIAGNOSIS USING BLOOD FLOW MAGNITUDE AND/OR DIRECTION

RELATED APPLICATION(S)

This application claims priority to U.S. Provisional Application No. 62/110,817 filed Feb. 2, 2015, the entire disclosure of which is hereby incorporated herein by reference in its entirety.

FIELD OF THE DISCLOSURE

Various embodiments of the present disclosure relate generally to disease assessment, treatment planning, and related methods. More specifically, particular embodiments of the present disclosure relate to systems and methods for diagnosing or performing treatment planning for vascular steal syndromes and/or retrograde flow.

BACKGROUND

Blood flow may sometimes deviate from an expected pattern. One example of blood flow deviation may include retrograde flow, a condition where a patient's blood flow may change direction. Stenoses or valve regurgitation may contribute to retrograde flow. Another example of blood flow deviation may include vascular steal syndromes, which may involve medical complications that may cause flow to increase in one part of the body at the expense of another. For example, vascular access-induced steal syndrome may include a condition where an arteriovenous (AV) fistula or graft may cause blood to flow through the access, "stealing" blood flow that would otherwise be delivered to the forearm or hand. Additional examples of these phenomena may include, e.g., subclavian steal syndrome, coronary steal syndrome, cardiac steal syndrome, dialysis access steal syndrome, iliac steal syndrome, aorto-iliac steal syndrome, renal-splanchnic steal syndrome, mesenteric arterial steal syndrome, splenic artery steal syndrome, and/or inter-splanchnic steal syndrome.

Retrograde flow and vascular steal syndromes may be dangerous to a patient. For instance, a diversion of expected blood flow to tissue from a vascular steal syndrome may cause blood supply inefficiency to that tissue, which may then lead to necrosis. Retrograde flow may cause or be linked to ischemia.

Meanwhile, harmful, blood flow deviation-related conditions may be hard to detect in advance. For example, vascular steal syndromes may be difficult to diagnose. Some vascular steal situations may occur only during certain physiological states (e.g., coronary steal syndrome) or result from moderate vascular disease. Thus, a desire exists to better understand the various pathological situations in a patient's vasculature and how they may cause or contribute to vascular steal syndromes or retrograde flow. More specifically, a desire exists for diagnosis and treatment of vascular steal syndromes and retrograde flow.

Furthermore, treatments or medical procedures may be associated with blood flow deviance. In other words, treatments or medical procedures performed to improve a patient's health, may incidentally impair or endanger the patient's health due to the treatment's impact on the patient's blood flow. For example, catheter flushing may cause retrograde flow and an arteriovenous (AV) fistula or graft may result in a vascular steal syndrome or retrograde blood flow. Thus, a desire also exists to identify a treatment that may resolve a flow deviance and/or help reduce or avoid a flow deviance. Specifically, a desire exists to ensure that a treatment may effectively address a vascular steal syndrome or, in the case of certain treatments (e.g., bypass graft), ensure that the treatment may not induce retrograde flow or a vascular steal syndrome as a byproduct of treatment.

The foregoing general description and the following detailed description are exemplary and explanatory only and are not restrictive of the disclosure.

SUMMARY

According to certain aspects of the present disclosure, systems and methods are disclosed for diagnosing and treatment planning for vascular steal syndromes and/or retrograde flow.

One method includes: receiving a reference blood flow direction at a location in a reference vasculature; determining a patient-related blood flow direction at a location in a patient's vasculature corresponding to the location in the reference vasculature; determining a difference in direction, between the reference blood flow direction of the reference vasculature and the patient-related blood flow direction of the patient's vasculature; and generating a representation of the location in the patient's vasculature associated with the difference in direction between the reference blood flow direction and the patient-related blood flow direction, or generating a treatment recommendation for the patient's vasculature based on the difference in direction between the reference blood flow direction and the patient-related blood flow direction.

In accordance with another embodiment, a system for determining blood flow deviation in a patient's vasculature comprises: a data storage device storing instructions for determining blood flow deviation in a patient's vasculature; and a processor configured for: receiving a reference blood flow direction at a location in a reference vasculature; determining a patient-related blood flow direction at a location in a patient's vasculature corresponding to the location in the reference vasculature; determining a difference in direction, between the reference blood flow direction of the reference vasculature and the patient-related blood flow direction of the patient's vasculature; and generating a representation of the location in the patient's vasculature associated with the difference in direction between the reference blood flow direction and the patient-related blood flow direction, or generating a treatment recommendation for the patient's vasculature based on the difference in direction between the reference blood flow direction and the patient-related blood flow direction.

In accordance with another embodiment, a non-transitory computer readable medium for use on a computer system containing computer-executable programming instructions for performing a method of determining blood flow deviation in a patient's vasculature, the method comprising: receiving a reference blood flow direction at a location in a reference vasculature; determining a patient-related blood flow direction at a location in a patient's vasculature corresponding to the location in the reference vasculature; determining a difference in direction, between the reference blood flow direction of the reference vasculature and the patient-related blood flow direction of the patient's vasculature; and generating a representation of the location in the patient's vasculature associated with the difference in direction between the reference blood flow direction and the patient-related blood flow direction, or generating a treatment recommendation for the patient's vasculature based on the difference in direction between the reference blood flow direction and the patient-related blood flow direction.

One method includes: receiving a reference relative blood flow magnitude comparing blood flow magnitude at a first location versus a second location in a reference vasculature; determining a first patient-related blood flow magnitude at a location in a patient's vasculature corresponding to the first location in the reference vasculature; determining a second patient-related blood flow magnitude at the location in a patient's vasculature corresponding to the second location in the reference vasculature; determining a patient-related relative blood flow magnitude by comparing the first patient-related blood flow magnitude to the second patient-related blood flow magnitude; comparing the reference relative blood flow magnitude and the patient-related relative blood flow magnitude; and at least one of: generating a representation of the patient's vasculature based on the difference between the reference relative blood flow magnitude and the patient-related relative blood flow magnitude, or generating a treatment recommendation for the patient's vasculature based on the difference between the reference relative blood flow magnitude and the patient-related relative blood flow magnitude.

In accordance with another embodiment, a system for determining blood flow deviation in a patient's vasculature comprises: a data storage device storing instructions for determining blood flow deviation in a patient's vasculature; and a processor configured for: receiving a reference relative blood flow magnitude comparing blood flow magnitude at a first location versus a second location in a reference vasculature; determining a first patient-related blood flow magnitude at a location in a patient's vasculature corresponding to the first location in the reference vasculature; determining a second patient-related blood flow magnitude at the location in a patient's vasculature corresponding to the second location in the reference vasculature; determining a patient-related relative blood flow magnitude by comparing the first patient-related blood flow magnitude to the second patient-related blood flow magnitude; comparing the reference relative blood flow magnitude and the patient-related relative blood flow magnitude; and at least one of: generating a representation of the patient's vasculature based on the difference between the reference relative blood flow magnitude and the patient-related relative blood flow magnitude, or generating a treatment recommendation for the patient's vasculature based on the difference between the reference relative blood flow magnitude and the patient-related relative blood flow magnitude.

In accordance with another embodiment, a non-transitory computer readable medium for use on a computer system containing computer-executable programming instructions for performing a method of determining blood flow deviation in a patient's vasculature, the method comprising: a reference relative blood flow magnitude comparing blood flow magnitude at a first location versus a second location in a reference vasculature; determining a first patient-related blood flow magnitude at a location in a patient's vasculature corresponding to the first location in the reference vasculature; determining a second patient-related blood flow magnitude at the location in a patient's vasculature corresponding to the second location in the reference vasculature; determining a patient-related relative blood flow magnitude by comparing the first patient-related blood flow magnitude to the second patient-related blood flow magnitude; comparing the reference relative blood flow magnitude and the patient-related relative blood flow magnitude; and at least one of: generating a representation of the patient's vasculature based on the difference between the reference relative blood flow magnitude and the patient-related relative blood flow magnitude, or generating a treatment recommendation for the patient's vasculature based on the difference between the reference relative blood flow magnitude and the patient-related relative blood flow magnitude.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

Blood flow in the body may change or deviate from an expected pattern. Such deviations may be harmful to a patient, yet difficult to detect in advance. For example, various pathological situations in a patient's vasculature may cause retrograde flow or vascular steal syndrome. This may mean, for instance, that the effect of vascular steal syndrome may not arise, unless a patient is in a particular physiological state. For example, a patient with subclavian steal syndrome may suddenly faint or develop neurologic deficits when the patient is at a particular pathological state (e.g., during exercise), while the patient may appear normal or healthy in other pathological conditions (e.g., at rest or during moderate activity). The exemplary symptoms of fainting or developing neurologic deficits may be caused by the way that blood is flowing due to the subclavian steal syndrome. Subclavian steal syndrome is described in more detail in FIG. 1A.

Figure 1A:
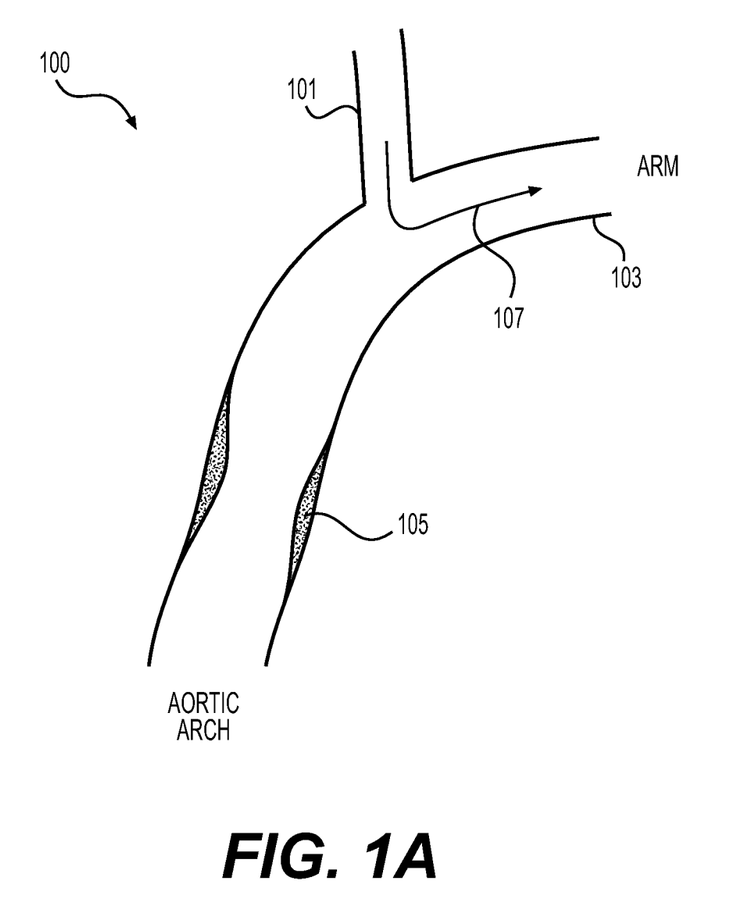
FIG. 1A is an exemplary schematic depiction of vascular steal syndrome, according to an exemplary embodiment of the present disclosure.

FIG. 1A is a schematic depiction of an exemplary vascular model 100 of a patient exhibiting a vascular steal syndrome, specifically, a subclavian steal syndrome, according to an exemplary embodiment of the present disclosure. Vascular model 100 may include a vertebral artery 101 and a subclavian artery 103. The illustrated subclavian artery 103 may include an occlusion or proximal stenosis 105. A normal blood flow may flow from the vertebral artery 101, down through the portion of the subclavian artery 103 where the occlusion or proximal stenosis 105 is pictured. Subclavian steal syndrome may exist where blood flow 107 travels in the (retrograde) direction of the arm, rather than through the subclavian artery 103 in the direction of normal blood flow, i.e., toward the stenosis 105. In some cases, a blockage (e.g., occlusion or proximal stenosis 105) may cause the deviant blood flow 107. In other words, the arm, in this situation, "steals" blood from the flow of blood that is expected to travel through the proximal subclavian artery for a normal, healthy patient.

Medical conditions that are expressed only during some pathological states may be difficult to diagnose because occurrence is inconsistent and there is no way to measure blood flow deviation from blood vessels or patient anatomy.

Therefore, an understanding of locations of deviant flow may be clinically important. The present disclosure may aid the diagnosis and treatment of vascular steal syndromes and retrograde flow by identifying area(s) of a patient's vasculature with deviant flow magnitude and/or direction. In addition, the present disclosure may provide systems and methods for virtually exploring various treatment strategies. In this way, the present disclosure provides systems and methods for identifying a treatment that may resolve the flow deviancy. In one such embodiment, a comparison of various treatment strategies may be used to select an optimal treatment that may resolve the flow deviancy.

Figure 1B:
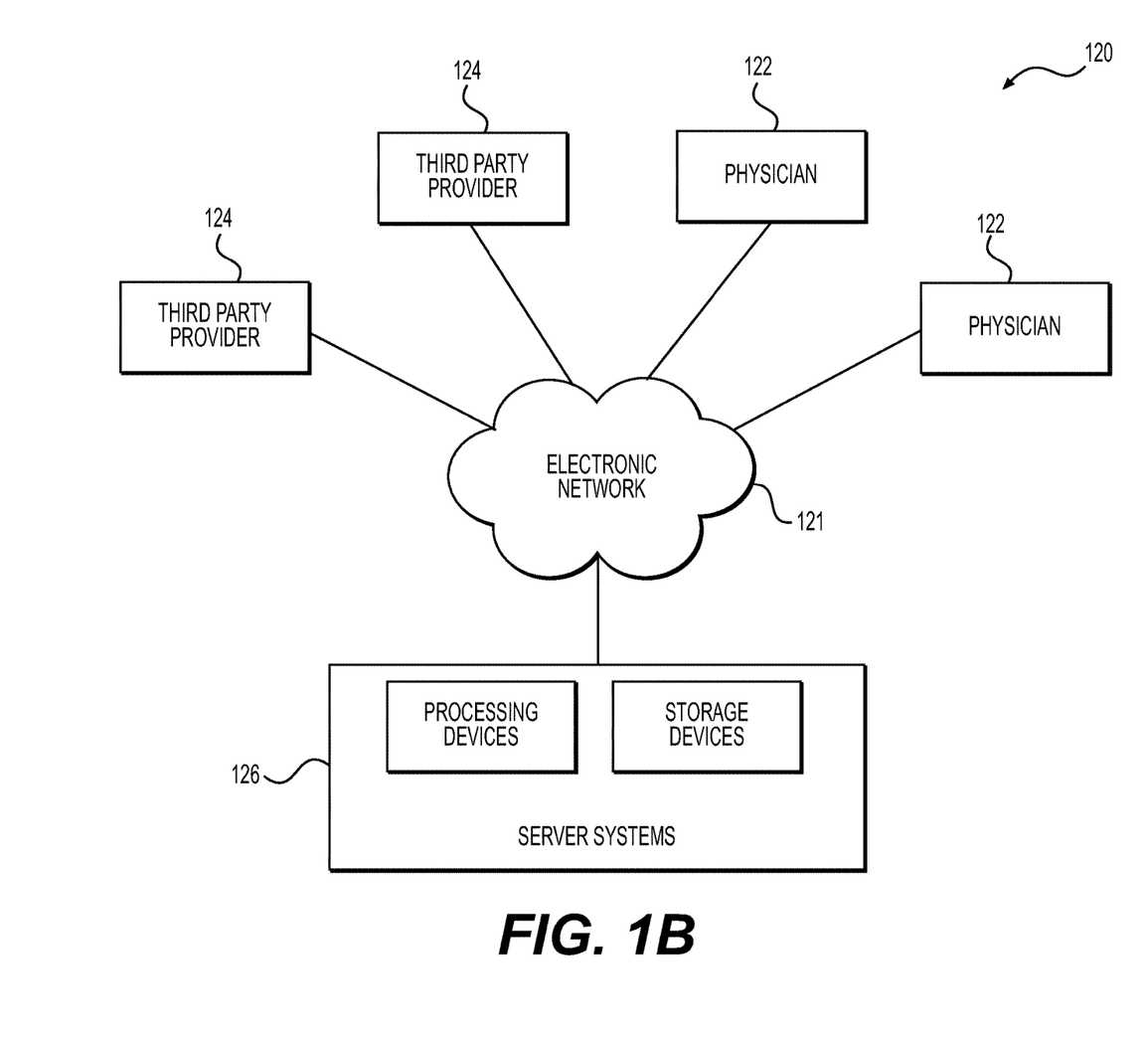
FIG. 1B is a block diagram of an exemplary system and network diagnosing or performing treatment planning for vascular steal syndromes and/or retrograde flow, according to an exemplary embodiment of the present disclosure.

FIG. 1B depicts a block diagram of an exemplary system 120 and network for diagnosing or performing treatment planning for vascular steal syndromes and/or retrograde flow, according to an exemplary embodiment. Specifically, FIG. 1B depicts a plurality of physicians 122 and third party providers 124, any of whom may be connected to an electronic network 121, for example, the Internet, through one or more computers, servers, and/or handheld mobile devices. Physicians 122 and/or third party providers 124 may create or otherwise obtain images of one or more patients' anatomy. The physicians 122 and/or third party providers 124 may also obtain any combination of patient-specific information, for example, age, medical history, blood pressure, blood viscosity, patient activity or exercise level, etc. Physicians 122 and/or third party providers 124 may transmit the anatomical images and/or patient-specific information to server systems 126 over the electronic network 121. Server systems 126 may include storage devices for storing images and data received from physicians 122 and/or third party providers 124. Server systems 126 may also include processing devices for processing images and data stored in the storage devices. For the present disclosure, "patient" may refer to any individual of interest.

Figure 2:
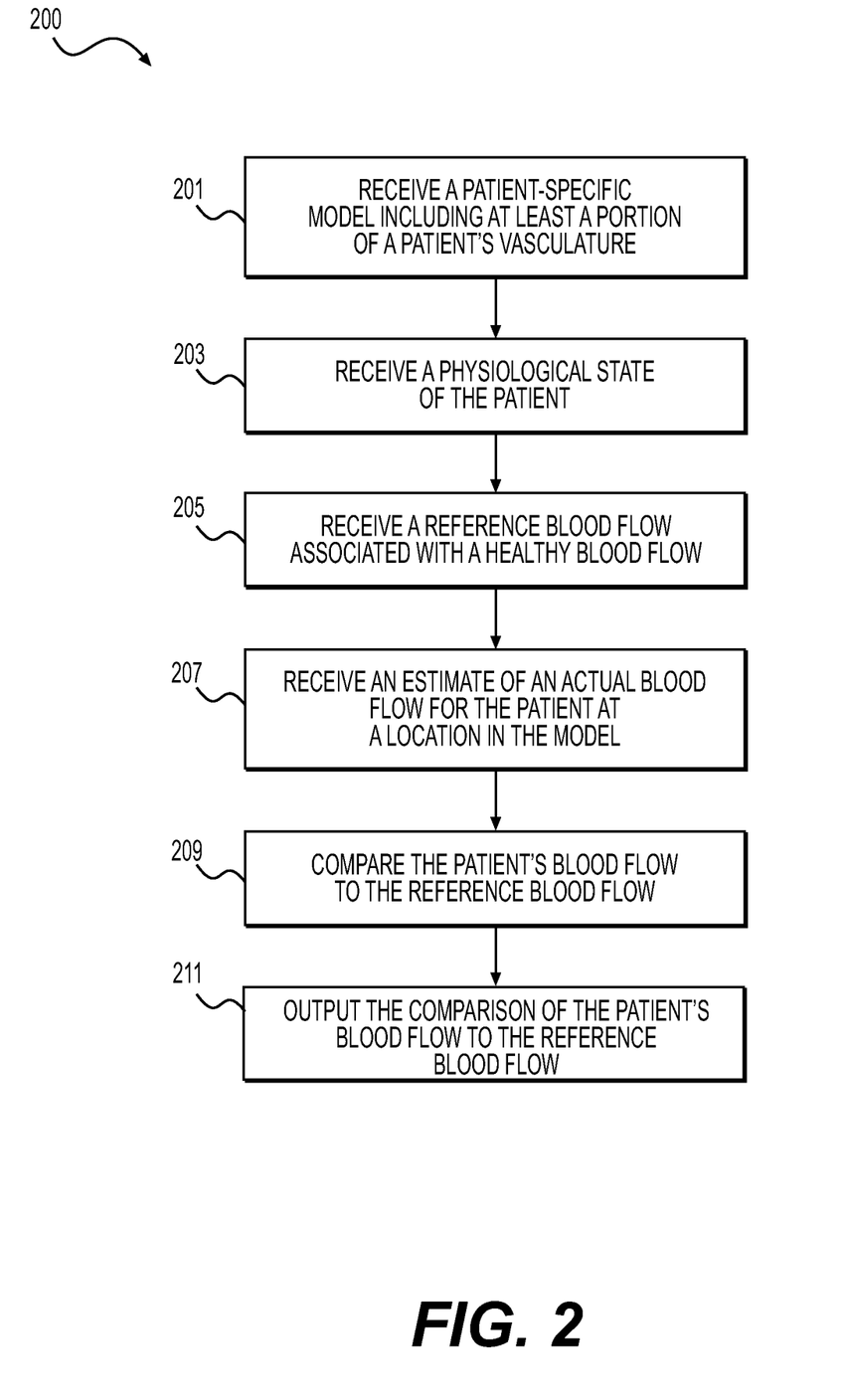
FIG. 2 is a block diagram of an exemplary method of diagnosing or performing treatment planning for vascular steal syndromes and/or retrograde flow, according to an exemplary embodiment of the present disclosure.
Figure 3A:
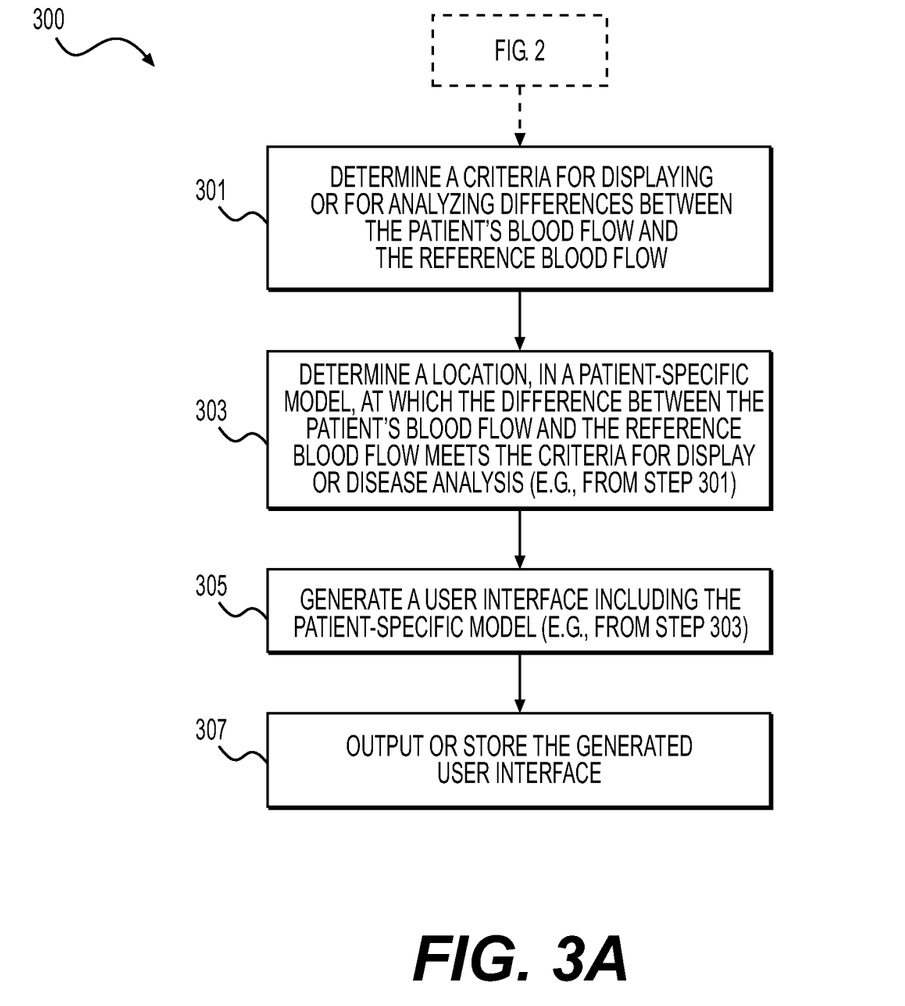
FIG. 3A is a block diagram of an exemplary method of locating areas of vascular steal syndromes and/or retrograde flow, according to an exemplary embodiment of the present disclosure.
Figure 3B:
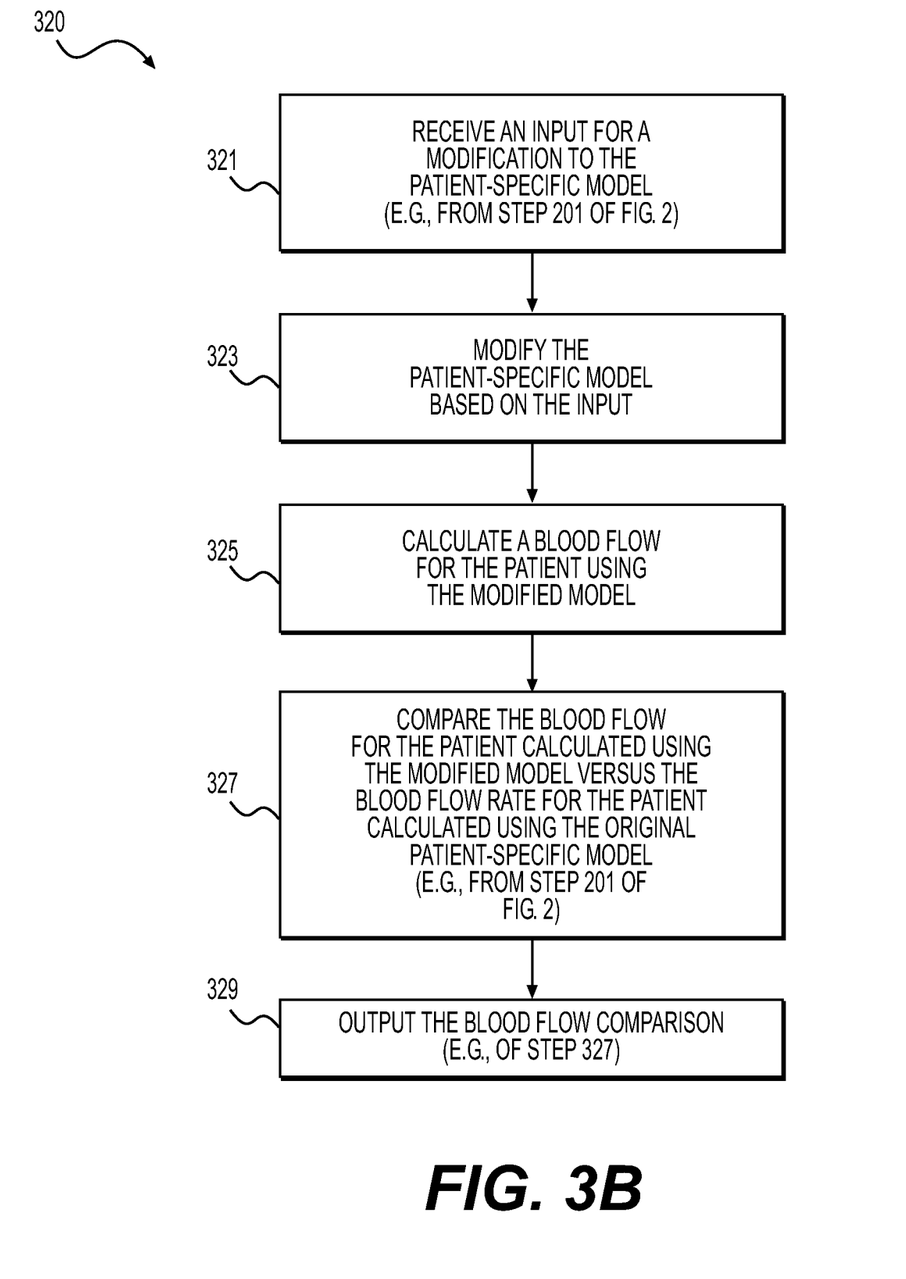
FIG. 3B is a block diagram of an exemplary method of comparing treatments related to vascular steal syndromes and/or retrograde flow, according to an exemplary embodiment of the present disclosure.

FIG. 2 depicts a general embodiment of a method for diagnosing or performing treatment planning for vascular steal syndromes and/or retrograde flow. For example, FIG. 2 includes a method for detecting retrograde flow or blood flow "stealing" that may occur in at least a portion of patient's circulatory system. FIGS. 3A and 3B include two methods of displaying or processing results of the analysis in the method of FIG. 2. For example, FIG. 3A depicts an embodiment of a process for locating areas of a patient's vasculature that may be associated with detected retrograde flow or blood flow "stealing." Locations in a patient's vasculature that may be associated with flow deviation (or vascular steal syndrome/retrograde flow), may be related to effective treatment locations in the patient's vasculature. For example, the method of FIG. 3A may include recommending treatment at one or more of the locations in the patient's vasculature associated with deviant blood flow.

FIG. 3B depicts an embodiment of a process for comparing treatments related to vascular steal syndromes and/or retrograde flow. As previously discussed, treatments may address, or in some cases even cause, one or more vascular steal syndromes and/or retrograde flow. In one embodiment, the method of FIG. 3B may be used to assess a single treatment. For example, the treatment may include a treatment for vascular steal syndrome or retrograde flow. In such a case, the assessment may include evaluating the treatment's efficacy in treating the patient's vascular steal syndrome or retrograde flow. In another instance, the treatment may include a treatment for a condition, other than vascular steal syndrome or retrograde flow, that may impact the patient. In such a case, the assessment may include evaluating the treatment to determine the likelihood or risk that the treatment may result in vascular steal syndrome or retrograde flow for the patient. Furthermore, the method of FIG. 3B may be used to find an optimal treatment for a patient, given the comparison of multiple treatments. Again, finding the optimal treatment may apply to the scenario of selecting an optimal treatment for treating one or more blood flow deviations, or the scenario of finding a treatment that has a lower likelihood of causing blood flow deviations that may harm the patient. The methods of FIGS. 3A and 3B may be performed together or separately.

FIG. 2 is a block diagram of an exemplary method 200 of diagnosing or performing treatment planning for vascular steal syndromes and/or retrograde flow, according to an exemplary embodiment. The method of FIG. 2 may be performed by server systems 126, based on information, images, and data received from physicians 122 and/or third party providers 124 over electronic network 121. Blood flow parameters (e.g., blood flow magnitude and/or blood flow direction) may indicate, or impact, a patient's health and medical condition. Method 200 may include a method of evaluating discrepancies between a patient's blood flow and healthy blood flow to diagnose blood flow-related scenarios (e.g., vascular steal syndromes and/or retrograde flow) and/or to inform treatment planning for such blood flow-related scenarios.

In one embodiment, step 201 may include receiving a patient-specific anatomical model including at least a portion of the patient's vasculature. In one embodiment, the patient-specific anatomic model may have been generated based on patient-specific imaging. Various imaging modalities may provide patient anatomy for the anatomic model e.g., computed tomography (CT) images (or scans), magnetic resonance imaging (MRI), ultrasound, angiography, etc. The imaging may include representations of a patient's coronary vasculature, cerebral vasculature, peripheral vasculature, renal vasculature, or visceral vasculature. The patient-specific anatomical model may be received in an electronic storage medium (e.g., hard drive, network drive, smart phone, tablet, cloud drive, etc.). For example, a third party vendor may provide the images. In one embodiment, the patient-specific anatomical model may include, e.g., a 3D geometrical model (e.g., a triangulated surface mesh) of the patient's arterial vasculature or a 1D geometrical model of the patient's arterial vasculature. The modeled patient vasculature may include any vasculature in a patient's body, including but not limited to one or more of: coronary vasculature, cerebral vasculature, peripheral vasculature, renal vasculature, visceral vasculature, etc.

In one embodiment, step 203 may include receiving a physiological state of the patient, e.g., a resting state, an exercise state, fasting, a hyperemic state, a postprandial, etc. The physiological state may include a designated physiological state, for instance, a physiological state at which the blood flow analysis of method 200 may take place. In other words, the remaining steps of method 200 involving reference blood flow or the patient's actual blood flow may relate to blood flow at the physiological state received (e.g., designated) in step 203. For example, an exercise state may correspond to a reference blood flow and an actual patient blood flow higher than a resting state reference blood flow or a resting state actual patient blood flow. Determining a physiological state of the patient in a blood flow analysis may provide context for a comparison of expected blood flow versus patient blood flow, so that patient blood flow and reference blood flow are blood flows associated with the same physiological state.

Furthermore, step 203 may permit comparison of blood flow deviations at various physiological states. For example, deviant flow may arise in some physiological states, and not in other physiological states. Identifying a physiological state as the basis of a blood flow analysis may permit comparison of blood flow characteristics from one state to another. For instance, a comparison of healthy blood flow versus actual (e.g., patient) blood flow during a resting state may contrast from a comparison of healthy blood flow versus actual blood flow during an exercise state.

By extension, changes in physiological state may be observed from blood flow. In one embodiment, step 203 may further include determining the physiological state of the patient. For example, step 203 may include identifying or defining one or more physiological states and determining that the patient's physical condition is associated with one or more of the identified or defined physiological states. In such a case, step 203 may further include selecting a physiological state for the patient, based on the physiological state(s) determined to be associated with the patient physical condition.

In one embodiment, step 205 may include receiving and/or determining a reference blood flow. In one embodiment, receiving the reference blood flow may include determining (e.g., estimating or measuring) the reference blood flow. For example, the reference blood flow may include an estimate of blood flow at one or more locations in the patient-specific anatomical model, at one anatomical/disease state, or at a physiological state (e.g., the received physiological state or a physiological state other than the received physiological state). The estimation of blood flow may include, for example, estimated blood flow magnitude and/or estimated blood flow direction. Anatomical/disease states may include, for example, blood flow for the patient in a healthy state or blood flow from an anatomical model of the patient at a prior time (e.g., using a pre-modification patient-specific model or a post-modification patient-specific model). Modifications may include geometric changes to the patient-specific model and/or changes to a blood flow, for example, opening or closing a vessel lumen in the anatomical model, revascularization in the anatomical model with a bypass graft, modifying the simulated physiological state, opening a total occlusion, etc.

In one embodiment, step 205 may include determining the reference blood flow using a known and population-based healthy blood flow, a known and population-based diseased blood flow, and/or a patient-specific healthy blood flow. In one embodiment, the known or population-based blood flows may include pre-set or standard reference blood flow values. Alternately or in addition, known and population-based blood flows may be obtained using, for example, machine learning or stored information. In some cases, the machine learning or stored information may be related to patient information so that the reference blood flow is tailored to the patient.

To explain further, step 205 of determining the reference blood flow may additionally include receiving patient information (e.g., patient-specific information described for FIG. 1B, including patient age, sex, medical history, physiological state, etc.). In one embodiment, machine learning may include building a collection of blood flow-related data (e.g., boundary conditions for flow simulations, geometry of modeled anatomy, etc.) pertaining to one or more individuals. Machine learning may include iteratively calculating blood flow using the blood flow-related data, to create simulations that characterize blood flow at a given set of conditions, e.g., patient age, sex, health condition, physiological state, medical history, etc. In other words, machine learning may provide reliable estimates of reference blood flow for a particular input, e.g., input for individuals similar to the patient.

Stored information may include information in a database. Step 205 may include selecting, from a variety of databases, a database containing blood flow information for individuals with characteristics that are similar to the received patient information. The database may include known (e.g., measured or simulated) examples of the blood flow characteristic. Such examples of the blood flow characteristic may be associated with one or more other patients and/or a population-based study, for example. The simulated examples may be derived from the machine-learning methods described earlier.

A patient-specific healthy blood flow may be obtained, for example, by detecting and removing disease elements from the patient-specific anatomical model and/or by estimating the patient-specific healthy blood flow using the patient-specific anatomical model. Estimating the patient-specific healthy blood flow may include, for instance, performing a 1D or 3D blood flow simulation, e.g., using a machine learning technique to estimate blood flow at a location (e.g., using a database of blood flow rates from similar healthy patients at similar locations). For example, the simulation may include using a different anatomical model of the patient. Examples of such an anatomical model may include a modified version of the received patient-specific anatomic model, or a model determined prior to the received model (e.g., showing the patient at a different time or physiological state from the time or physiological state associated with the received model). Alternately or in addition, the simulation may include using a pre-treatment blood flow (e.g., in which the treatment may be virtual or actual). Furthermore, the simulation may include a physics-based or reduced-order model for simulating the blood flow (e.g., using computational fluid dynamics). Parameters of the simulation may be adjusted to model blood flow at various physiological states.

In one embodiment, step 207 may include receiving an estimate of actual blood flow for the patient at one or more locations in the patient-specific anatomical model. In one embodiment, step 207 may include receiving an actual patient blood flow by determining an estimate of the patient's actual blood flow rate. For example, estimating the actual flow rate may include measuring the actual flow rate from invasive measurements or noninvasive imaging, performing a 0D, 1D or 3D blood flow simulation, using a machine learning technique to estimate blood flow at a location, etc. Invasive measurements may include measurements found using a pressure wire. Noninvasive imaging may include Doppler ultrasound or magnetic resonance imaging (MRI). An exemplary machine learning technique may include using a database of blood flow rates from similar patients, at similar locations of the respective patients' vasculature. In one embodiment, the estimated, actual blood flow rate for the patient may be associated with the received physiological state (e.g., from step 203).

In one embodiment, step 209 may include determining, using a processor (e.g., a computer, laptop, tablet, smart phone, digital signal processing (DSP), cloud computer, graphics processing unit), a comparison of the patient's actual blood flow rate at a location in the patient-specific model to the reference blood flow rate at a location of a vasculature corresponding to the location in the patient-specific model. Such a comparison may be made for blood flow at multiple locations in the patient-specific model. In one embodiment, the comparison of step 209 may include comparing the blood flow direction (e.g., by determining the inner product velocity vectors) and/or the blood flow magnitude (e.g., by taking an absolute difference or squared difference) for the reference blood flow rate versus the patient's actual blood flow rate.

In one embodiment, step 211 may include outputting the comparison to an electronic storage medium or electronic display. For example, the comparison may be shown as a graphical, numerical, and/or pictorial display. In one embodiment, the comparison of step 211 may be sufficient to diagnose a steal syndrome or retrograde flow. For instance, step 211 may prompt a diagnosis of disease where the difference between the patient's actual blood flow and the reference blood flow exceeds a given threshold.

In another alternate or additional embodiment, the comparison of step 211 may include a comparison of relative blood flow, e.g., relative blood flow magnitude. For example, since step 207 may include receiving an estimate of actual blood flow magnitude for the patient ($M_P$) at one or more locations in the patient-specific anatomical model, one embodiment of method 200 may include comparing an estimate of patient blood flow magnitude at a first location (e.g., $L_{P1}$) in the patient's vasculature against an estimate of patient blood flow magnitude at a second location (e.g., $L_{P2}$) in the patient's vasculature. The patient blood flow may be characterized as, for instance, $$M_P=(M_{LP1}M_{LP2})$$

In such an embodiment, the reference blood flow may also include a relative measurement, e.g., reference blood flow at location ($L_{R1}$) corresponding to the first location ($L_{P1}$) of the patient's vasculature versus reference blood flow at a location ($L_{R2}$) corresponding to the second location ($L_{P2}$) of the patient's vasculature. In other words, reference relative blood flow may be characterized as, $$M_R=(M_{LR1}M_{LR2})$$

$M_R$ may include the difference in blood flow magnitude between one selected location in a vasculature versus a second selected location in the vasculature of a healthy individual. In one embodiment, the relative measurement may include a difference in measurements, e.g., as described above with $M_P$ and $M_R$. In another exemplary embodiment, the relative measurement may include a ratio of measurements, e.g., where $M_P=(M_{LP1}/M_{LP2})$ and $M_R=(M_{LR1}/M_{LR2})$.

A difference between $M_P$ and $M_R$ may indicate a steal syndrome in the patient's vasculature. In other words, a patient relative blood flow magnitude may deviate from an expected or healthy relative blood flow magnitude because an amount of blood is being "stolen." Accordingly, a comparison of relative blood flow (or blood flow magnitude) may provide a diagnosis for steal syndrome.

For example, a diagnosis for subclavian steal syndrome may include $M_P=(M_{LP1} M_{LP2})$ where $L_{P1}$ a location in the subclavian artery and $Lp_2$ a location in the vertebral artery. In such a scenario, vascular steal syndrome may be indicated where $M_P>M_R$, since subclavian steal syndrome may involve the subclavian artery location ($L_{P1}$) "stealing" blood flow from the vertebral artery location ($L_{P2}$). In another scenario, $L_{P1}$ may be located in the vertebral artery and $L_{P2}$ may be located in the aortic arch, downstream of the vertebral artery. Then, $M_P<M_R$ may indicate subclavian steal syndrome, where a magnitude of blood flow through the aortic arch is lower than in a healthy individual, since blood flow is being "stolen" by the vertebral artery. The locations $L_{P1}$ and $L_{P2}$ in a vasculature may influence the predetermined relationship or threshold difference between $M_P$ and $M_R$ that may be identified or defined for prompting a diagnosis.

Furthermore, the difference between $M_P$ and $M_R$, or the ratio, $M_P:M_R$, may be compared to a threshold value that may be indicative of steal syndrome. For example, an individual may be healthy if $M_P:M_R=1$, meaning the patient's blood flow matches that of a healthy, reference blood flow. A ratio greater than 1.3 or less than 0.7, for example, may indicate an "unhealthy stealing" of blood from one vessel to another vessel. Threshold values, in such a case, may include, for example, 1.3 as a maximum threshold and 0.7 as a minimum threshold.

In yet another alternate or additional embodiment, method 200 may be performed for various physiological states so that the output comparison (e.g., from step 211) may be analyzed across a plurality of physiological states. In some scenarios, retrograde flow or "stealing" of blood (related to a vascular steal syndrome), for instance, may occur only in some physiological states. Comparing the output of step 211 for more than one physiological state may permit identification of a physiological state where a patient may experience retrograde flow or "stealing" of blood. In one embodiment, such information may pertain only to the patient. Alternately or in addition, such information may be useful for extrapolating information for a population of individuals, e.g., individuals that may share similar patient characteristics (e.g., medical history, age, gender, physical condition, etc.). The association may permit a recommendation as to physiological states that a patient (or individuals similar to the patient) should be cautious of, or avoid. For example, if the patient blood flow varies drastically from a reference blood flow for a patient while the patient engages in rigorous exercise, the association in step 211 may further prompt a recommendation for the patient to try to avoid rigorous exercise.

FIG. 3A is a block diagram of an exemplary method 300 of locating areas of vascular steal syndromes and/or retrograde flow, according to an exemplary embodiment. The method of FIG. 3A may be performed by server systems 126, based on information, images, and data received from physicians 122 and/or third party providers 124 over electronic network 121.

As previously discussed, deviant blood flow may include instances of discrepancies between a patient's blood flow and a reference (e.g., healthy) blood flow. For example, the difference in blood flow direction may be determined, in an exemplary case, where the inner product of the blood flow rate velocity vector of the reference blood flow rate and the velocity vector of the actual blood flow rate is less than zero. In some cases, only a subset of the deviant blood flow may be significant for disease analysis. Method 300 may include isolating, from the comparison performed in method 200, a subset of deviant blood flow for disease analysis. In one embodiment, method 300 may include displaying the subset of deviant blood flow.

In one embodiment, step 301 may include defining a standard or criteria for the deviant blood flow to display to a user, e.g., a user performing or using such a disease analysis. One standard may include displaying a difference between an actual blood flow magnitude and a reference blood flow magnitude that exceeds a predetermined threshold (e.g., 1.3 or 0.7, as described for step 207). Another standard may include displaying a difference, between an actual blood flow magnitude and a reference blood flow magnitude, that may be a statistical outlier among computed differences. Similar standards regarding predetermined thresholds or statistical outliers may apply to relative blood flow magnitudes.

In one embodiment, step 303 may include determining deviant blood flow within a patient's vasculature (e.g., from step 207 or step 211) that meets a criteria for display and/or disease analysis (e.g., from step 301). For example, step 303 may include determining one or more locations in the patient's vasculature where the difference between the patient's blood flow magnitude and a reference blood flow magnitude is a statistical outlier among computed differences. Step 303 may further include determining varying grades or levels of severity in the deviation between the reference blood flow and the patient blood flow.

In one embodiment, step 305 may include generating a user interface displaying the determined deviant blood flow within the patient's vasculature, e.g., on a representation of the patient-specific model. For example, step 305 may include outputting a display including a representation of the patient-specific model, with the areas of deviant blood flow shown (e.g., via highlighting, color, or any type of visual signifier). In one embodiment, the display or representation generated in step 305 may also distinguish between varying degrees or extents of deviation between the reference blood flow and actual blood flow. For example, locations of the patient vasculature that experience high deviation may be marked yellow in the representation, while locations with low deviation may be marked as green in the representation. The display may be output or stored on an electronic medium or electronic display (step 307).

FIG. 3B is a block diagram of an exemplary method 320 of comparing treatments for vascular steal syndromes and/or retrograde flow, according to an exemplary embodiment. The method of FIG. 3B may be performed by server systems 126, based on information, images, and data received from physicians 122 and/or third party providers 124 over electronic network 121.

In one embodiment, step 321 may include receiving an input for a modification to the patient-specific model, e.g., a geometrical modification and/or a physiological state change. Modifications to the patient-specific model may reflect multiple different treatments or disease progressions. Exemplary modifications may include, for example, narrowing a portion of vasculature in the patient-specific anatomic model at a location to reflect disease progression, modifying a portion of vasculature in the patient-specific model to show varying levels of blockage at one or more locations in the patient's vasculature to reflect the onset or introduction of an occlusion or resection, widening the vascular model at a location to reflect disease regression, widening a portion of vasculature in the patient-specific anatomic model at a location in the model to reflect a virtual stent (or other device to widen the vessel), adding one or more additional branches to a portion of vasculature in the patient-specific anatomic model to reflect a bypass, etc.

In one embodiment, step 323 may include modifying the patient-specific model, based on the received input for the modification. Step 323 may further include generating a representation of the modification and/or prompting a validation or further selection related to the modification. For example, if the modification includes modeling disease progression, step 323 may include generating a prompt for a user to select location(s) of the patient-specific model in which to observe the disease progression, and generating a further prompt requesting a range of time or level of progression to analyze and/or display.

In one embodiment, step 325 may include recalculating patient blood flow, based on the modifications (e.g., using the modified patient-specific model). The recalculations may be performed using one or more methods described, for example, at step 207 of method 200. In one embodiment, step 325 may further include updating reference blood flows, based on the received modification and/or the recalculation (e.g., to train an algorithm in generating accurate reference blood flow information).

In one embodiment, step 327 may include computing a comparison between the patient's blood flow pre-modification (e.g., from step 207 of method 200), and the patient's blood flow post-modification (e.g., from step 325).

In one embodiment, step 329 may include outputting results of the comparison to, e.g., an electronic storage medium. Such a comparison may be used for treatment planning. For example, an input may include a modification comprising an introduction of an occlusion or a widening in the patient's vasculature. One such case may include a modification introducing an occlusion at a first location in the patient's vasculature. Another input may include a modification comprising an introduction of an occlusion at a second location in the patient's vasculature. Blood flow estimates for each of the occlusion locations may be compared to reference blood flow rate(s). For example, the occlusion location that results in a patient blood flow with lower deviation from the reference blood flow, may be chosen as a treatment recommendation over the occlusion location that may cause a patient blood flow with higher deviation from the reference blood flow. Another case may include a modification introducing a widening at a first location in the patient's vasculature, and a widening at a second location in the patient's vasculature. Blood flow estimates for each of the widened locations may be compared to reference blood flow rate(s), and a location associated with lower deviation from the reference blood flow may be selected as a treatment site (over locations associated with higher deviation).

Blood flow that deviates from an expected, healthy blood flow sometimes impacts a patient health. For example, deviant blood flow may cause vascular steal syndromes, which may endanger a patient. Harmful patient conditions related to deviant blood flow may be difficult to detect, since the deviant blood flow may occur only under certain physiological states, or effects of the deviant blood flow may become more pronounced only under certain physiological states. The present disclosure may be useful in detecting deviant blood flow in advance, thus improving diagnoses for vascular steal syndromes and/or retrograde flow. In addition, a better understanding of deviant flow may improve treatment planning, either to better treat vascular steal syndromes and/or retrograde flow or to better select treatments for a patient that are less likely to later induce vascular steal syndromes and/or retrograde flow.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of determining blood flow deviation in a patient's vasculature, the method comprising:
   receiving an electronic representation of a reference vasculature from a population-based healthy blood flow vasculature or a population-based diseased blood flow vasculature;
   receiving a patient-specific model of a patient's vasculature representing a patient-specific healthy blood flow vasculature or a patient-specific diseased blood flow vasculature, wherein the patient's vasculature and the reference vasculature are of at least a common anatomical region and physiological state;
   determining a reference blood flow direction at a location in the reference vasculature using the electronic representation of the reference vasculature;
   simulating a blood flow through the patient-specific model;
   computing a simulated patient-related blood flow direction at a location in the patient's vasculature corresponding to the location in the reference vasculature, using the simulated blood flow through the patient-specific model of the patient's vasculature, the reference vasculature being different from the patient vasculature;
   determining a simulated patient-specific blood flow deviation, based on a calculated difference in direction between the reference blood flow direction of the reference vasculature at a plurality of locations and the simulated patient-related blood flow direction of the patient's vasculature corresponding to each of the plurality of locations; and
   based on whether the simulated patient-specific blood flow deviation includes a statistical outlier based on the calculated difference at at least one of the plurality of locations, generating
      a treatment recommendation for treating each of the plurality of locations of the simulated patient-specific blood flow having the deviation.

2. The computer-implemented method of claim 1, further comprising:
   receiving a physiological state associated with the patient;
   determining the reference blood flow direction based on the physiological state; and
   computing the simulated patient-specific blood flow direction further based on the physiological state.

3. The computer-implemented method of claim 1, wherein computing the simulated patient-specific blood flow direction comprises estimating blood flow through the location in the patient's vasculature corresponding to the location in the reference vasculature.

4. The computer-implemented method of claim 3, further comprising:
   determining one or more areas of the patient-specific anatomic model associated with the simulated patient-specific blood flow deviation; and
   generating a visual representation based on the one or more areas of the patient-specific anatomic model associated with the simulated patient-specific blood flow deviation.

5. The computer-implemented method of claim 1, further comprising:
   generating a visual representation of the location in the patient's vasculature; and
   generating the treatment recommendation.

6. The computer-implemented method of claim 1, further comprising:
   determining a second patient-related blood flow direction at the location in the patient's vasculature corresponding to the location in the reference vasculature, wherein determining the second patient-related blood flow direction includes simulating or estimating blood flow through the location in the patient's vasculature; and
   comparing the reference blood flow direction to the second patient-related blood flow direction to determine a difference in direction between the reference blood flow direction of the reference vasculature and the second patient-related blood flow direction of the patient's vasculature.

7. The computer-implemented method of claim 6, further comprising:
   generating the treatment recommendation for the simulated blood flow deviation, further based on a comparison of the difference in direction between the reference blood flow direction and the simulated patient-specific blood flow direction against the difference in direction between the reference blood flow and the second patient-related blood flow direction.

8. The computer-implemented method of claim 6, wherein the simulation for the second patient-related blood flow direction includes a vascular geometry different from the geometry of the patient's vasculature or a physiological state different from the physiological state at which the simulated patient-specific blood flow direction is determined.

9. A system for determining blood flow deviation in a patient's vasculature, the system comprising:
   at least one data storage device storing instructions for determining blood flow deviation in a patient's vasculature; and
   at least one processor configured to execute the instructions to perform a method including:
      receiving an electronic representation of a reference vasculature from a population-based healthy blood flow vasculature or a population-based diseased blood flow vasculature;
      receiving a patient-specific model of a patient's vasculature representing a patient-specific healthy blood flow vasculature or a patient-specific diseased blood flow vasculature, wherein the patient's vasculature and the reference vasculature are of at least a common anatomical region and physiological state;
      determining a reference blood flow direction at a location in the reference vasculature using the electronic representation of the reference vasculature;

simulating a blood flow through the patient-specific model;

computing a simulated patient-related blood flow direction at a location in the patient's vasculature corresponding to the location in the reference vasculature, using the simulated blood flow through the patient-specific model of the patient's vasculature, the reference vasculature being different from the patient vasculature;

determining a simulated patient-specific blood flow deviation, based on a difference in direction between the reference blood flow direction of the reference vasculature at a plurality of locations and the simulated patient-related blood flow direction of the patient's vasculature corresponding to each of the plurality of locations; and based on whether the simulated patient-specific blood flow deviation includes a statistical outlier based on the calculated difference at at least one of the plurality of locations, generating a treatment recommendation for treating each of the plurality of locations of the simulated patient-specific blood flow having the deviation.

10. The system of claim 9, wherein the system is further configured for:

receiving a physiological state associated with the patient;
determining the reference blood flow direction based on the physiological state; and
computing the simulated patient-specific blood flow direction further based on the physiological state.

11. The system of claim 9, wherein computing the simulated patient-specific blood flow direction comprises estimating blood flow through the location in the patient's vasculature corresponding to the location in the reference vasculature.

12. The system of claim 11, wherein the system is further configured for:

determining one or more areas of the patient-specific anatomic model associated with the simulated patient-specific blood flow deviation; and
generating a visual representation based on the one or more areas of the patient-specific anatomic model associated with the simulated patient-specific blood flow deviation.

13. The system of claim 9, wherein the system is further configured for:

generating a visual representation of the location in the patient's vasculature; and
generating the treatment recommendation.

14. The system of claim 13, wherein the system is further configured for:

determining a second patient-related blood flow direction at the location in the patient's vasculature corresponding to the location in the reference vasculature, wherein determining the second patient-related blood flow direction includes simulating or estimating blood flow through the location in the patient's vasculature; and
comparing the reference blood flow direction to the second patient-related blood flow direction to determine a difference in direction between the reference blood flow direction of the reference vasculature and the second patient-related blood flow direction of the patient's vasculature.

15. The system of claim 14, wherein the system is further configured for:

generating the treatment recommendation for the simulated blood flow deviation, further based on a comparison of the difference in direction between the reference blood flow direction and the simulated patient-specific blood flow direction against the difference in direction between the reference blood flow and the second patient-related blood flow direction.

16. The system of claim 14, wherein the simulation for the second patient-related blood flow direction includes a vascular geometry different from the geometry of the patient's vasculature or a physiological state different from the physiological state at which the simulated patient-specific blood flow direction is determined.

17. A non-transitory computer readable medium for use on a computer system containing computer-executable programming instructions for performing a method of determining blood flow deviation in a patient's vasculature, the method comprising:

receiving an electronic representation of a reference vasculature from a population-based healthy blood flow vasculature or a population-based diseased blood flow vasculature;
receiving a patient-specific model of a patient's vasculature representing a patient-specific healthy blood flow vasculature or a patient-specific diseased blood flow vasculature, wherein the patient's vasculature and the reference vasculature are of at least a common anatomical region and physiological state;
determining a reference blood flow direction at a location in the reference vasculature using the electronic representation of the reference vasculature;
simulating a blood flow through the patient-specific model;
computing a simulated patient-related blood flow direction at a location in the patient's vasculature corresponding to the location in the reference vasculature, using the simulated blood flow through the patient-specific model of the patient's vasculature, the reference vasculature being different from the patient vasculature;
determining a simulated patient-specific blood flow deviation, based on a difference in direction between the reference blood flow direction of the reference vasculature at a plurality of locations and the patient-related blood flow direction of the patient's vasculature corresponding to each of the plurality of locations; and
based on whether the simulated patient-specific blood flow deviation includes a statistical outlier based on the calculated difference at at least one of the plurality of locations, generating
a treatment recommendation for treating each of the plurality of locations of the simulated patient-specific blood flow having the deviation.

18. The non-transitory computer readable medium of claim 17, the method further comprising:

receiving a physiological state associated with the patient;
determining the reference blood flow direction based on the physiological state; and
computing the simulated patient-specific blood flow direction further based on the physiological state.

19. The non-transitory computer readable medium of claim 17, wherein computing the simulated patient-specific blood flow direction comprises estimating blood flow through the location in the patient's vasculature corresponding to the location in the reference vasculature.

20. The non-transitory computer readable medium of claim 17, the method further comprising:

generating a visual representation of the location in the patient's vasculature; and
generating the treatment recommendation.

* * * * *

UNITED STATES PATENT AND TRADEMARK OFFICE
CERTIFICATE OF CORRECTION

PATENT NO. : 10,987,010 B2
APPLICATION NO. : 14/691105
DATED : April 27, 2021
INVENTOR(S) : Leo Grady et al.

It is certified that error appears in the above-identified patent and that said Letters Patent is hereby corrected as shown below:

In the Claims

Column 13, Lines 33-35, in Claim 1, delete "determining a reference blood flow direction at a location in the reference vasculature using the electronic representation of the reference vasculature" and insert --determining a reference blood flow direction at each of a plurality of locations in the reference vasculature using the electronic representation of the reference vasculature--.

Column 13, Lines 38-55, in Claim 1, delete "computing a simulated patient-related blood flow direction at a location in the patient's vasculature corresponding to the location in the reference vasculature, using the simulated blood flow through the patient-specific model of the patient's vasculature, the reference vasculature being different from the patient vasculature; determining a simulated patient-specific blood flow deviation, based on a calculated difference in direction between the reference blood flow direction of the reference vasculature at a plurality of locations and the simulated patient-related blood flow direction of the patient's vasculature corresponding to each of the plurality of locations; and based on whether the simulated patient-specific blood flow deviation includes a statistical outlier based on the calculated difference at at least one of the plurality of locations, generating" and insert --computing a simulated patient-related blood flow direction at a plurality of locations in the patient's vasculature corresponding to the location in the reference vasculature using the simulated blood flow through the patient-specific model of the patient's vasculature, the reference vasculature being different from the patient vasculature; for each of the plurality of locations in the patient's vasculature, calculating a difference in direction between the simulated patient-related blood flow direction at the location in the patient's vasculature and the reference blood flow direction at the corresponding location in the reference vasculature; determining a simulated patient-specific blood flow deviation in the patient's vasculature based on the calculated difference at a location in the patient's vasculature being a statistical outlier among the plurality of calculated differences; and generating--.

Column 14, Lines 65-67, in Claim 9, delete "determining a reference blood flow direction at a Signed and Sealed this
Twenty-fourth Day of August, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,987,010 B2 location in the reference vasculature using the electronic representation of the reference vasculature" and insert --determining a reference blood flow direction at each of a plurality of locations in the reference vasculature using the electronic representation of the reference vasculature--.

Column 15, Lines 3-19, in Claim 9, delete "computing a simulated patient-related blood flow direction at a location in the patient's vasculature corresponding to the location in the reference vasculature, using the simulated blood flow through the patient-specific model of the patient's vasculature, the reference vasculature being different from the patient vasculature; determining a simulated patient-specific blood flow deviation, based on a difference in direction between the reference blood flow direction of the reference vasculature at a plurality of locations and the simulated patient-related blood flow direction of the patient's vasculature corresponding to each of the plurality of locations; and based on whether the simulated patient-specific blood flow deviation includes a statistical outlier based on the calculated difference at at least one of the plurality of locations, generating" and insert --computing a simulated patient-related blood flow direction at a plurality of locations in the patient's vasculature corresponding to the location in the reference vasculature using the simulated blood flow through the patient-specific model of the patient's vasculature, the reference vasculature being different from the patient vasculature; for each of the plurality of locations in the patient's vasculature, calculating a difference in direction between the simulated patient-related blood flow direction at the location in the patient's vasculature and the reference blood flow direction at the corresponding location in the reference vasculature; determining a simulated patient-specific blood flow deviation in the patient's vasculature based on the calculated difference at a location in the patient's vasculature being a statistical outlier among the plurality of calculated differences; and generating--.

Column 16, Lines 26-28, in Claim 17, delete "determining a reference blood flow direction at a location in the reference vasculature using the electronic representation of the reference vasculature" and insert --determining a reference blood flow direction at each of a plurality of locations in the reference vasculature using the electronic representation of the reference vasculature--.

Column 16, Lines 31-47, in Claim 17, delete "computing a simulated patient-related blood flow direction at a location in the patient's vasculature corresponding to the location in the reference vasculature, using the simulated blood flow through the patient-specific model of the patient's vasculature, the reference vasculature being different from the patient vasculature; determining a simulated patient-specific blood flow deviation, based on a difference in direction between the reference blood flow direction of the reference vasculature at a plurality of locations and the simulated patient-related blood flow direction of the patient's vasculature corresponding to each of the plurality of locations; and based on whether the simulated patient-specific blood flow deviation includes a statistical outlier based on the calculated difference at at least one of the plurality of locations, generating" and insert --computing a simulated patient-related blood flow direction at a plurality of locations in the patient's vasculature corresponding to the location in the reference vasculature using the simulated blood flow through the patient-specific model of the patient's vasculature, the reference vasculature being different from the patient vasculature; for each of the plurality of locations in the patient's vasculature, calculating a difference in direction between the simulated patient-related blood flow direction at the location in the patient's vasculature and the reference blood flow direction at the corresponding location in the reference vasculature; determining a simulated patient-specific blood flow deviation in the patient's vasculature based on the calculated difference at a location in the patient's vasculature being a statistical outlier among the plurality of calculated differences; and generating--.